(12) United States Patent
Grillo et al.

(10) Patent No.: US 6,348,090 B1
(45) Date of Patent: Feb. 19, 2002

(54) FILM COATINGS AND FILM COATING COMPOSITIONS BASED ON DEXTRIN

(75) Inventors: Susan M. Grillo; Brian Korchok, both of Lansdale; Bruce Kinsey, Harleysville; Stuart C. Porter, Hatfield; George Reyes, North Wales; Thomas J. Burke, Plymouth Meeting; Charles Cunningham, Ambler, all of PA (US)

(73) Assignee: BPSI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/661,655

(22) Filed: Sep. 14, 2000

Related U.S. Application Data (60) Division of application No. 09/002,462, filed on Jan. 2, 1998, now Pat. No. 6,183,808, which is a continuation-in-part of application No. 08/778,944, filed on Jan. 6, 1997, now abandoned.

(51) Int. Cl.⁷ .......................... C09D 103/02; C08L 3/02
(52) U.S. Cl. ................. 106/162.1; 106/205.01
(58) Field of Search .................. 106/162.1, 205.01, 106/205.8

(56) References Cited

U.S. PATENT DOCUMENTS

| | | | |
|---|---|---|---|
| 3,669,688 A | * 6/1972 | Thompson et al. | |
| 4,293,572 A | * 10/1981 | Silva et al. | 426/19 |
| 4,327,076 A | 4/1982 | Puglia et al. | |
| 4,384,005 A | 5/1983 | McSweeney | |
| 4,643,894 A | 2/1987 | Porter et al. | |
| 4,692,342 A | * 9/1987 | Gannis et al. | 426/293 |
| 4,762,721 A | * 8/1988 | Holscher et al. | 426/94 |
| 4,802,924 A | * 2/1989 | Woznicki et al. | 427/3 |
| 4,828,841 A | 5/1989 | Porter et al. | |
| 4,828,845 A | * 5/1989 | Zamudid-Tena et al. | 426/5 |
| 4,843,098 A | 6/1989 | Shaw et al. | |
| 4,981,707 A | * 1/1991 | Morris | 426/93 |
| 5,470,581 A | * 11/1995 | Grillo et al. | 424/479 |

FOREIGN PATENT DOCUMENTS

JP 5238107 * 9/1977

OTHER PUBLICATIONS

Panning Techniques: Hard Panning, Robert T. Strub (1987).
Science and Technology Third Edition, "Chocolate, Cocoa and Confectionery", Bernard W. Minifie (Published by Van Nestrand Reinhold, New York) (1989) pp. 221–223.
Edible Coatings and Films to Improve Food Quality, edited by John M. Krochta, Elizabeth A. Baldwin, and Myrna O. Nisperos–Carriedo (Published by Technomic Publishing Company, Inc.) (1994) (p. 317).
Dictionary of Food Ingredients, by Robert S. Igoe (Published by Van Nostrand Reinhold) (1989).
Brochure Entitled "Gum Arabic Replacers", National Starch and Chemcial Company (1995).
Technical Service Bulletin, National Starch and Chemical Company (199
Suesswaren, (1995), 39(4), 20–22.*
Kennedy's Confection, (1995), 2(3) 9, 11, 13.*
Food Engineering, 1972 44 (5) 88–90.*
Erma Cameron, Jul. 25, 2001.*

* cited by examiner

Primary Examiner—Erma Cameron
(74) Attorney, Agent, or Firm—Roberts & Mercanti, LLP (57) ABSTRACT

A dry film coating composition for forming a coating suspension for film coating nutritional supplements, pharmaceutical tablets, and the like, including tapica dextrin and a detackifier.

45 Claims, 7 Drawing Sheets

FILM COATINGS AND FILM COATING COMPOSITIONS BASED ON DEXTRIN

The present application is a divisional of U.S. Ser. No. 09/002,462, filed on Jan. 2, 1998, now U.S. Pat. No. 6,183,808 B1, which in turn is a continuation-in-part of U.S. Ser. No. 08/778,944, filed on Jan. 6, 1997, now abandoned, the contents of each of which are incorporated by reference herein in its entirety.

BACKGROUND OF THE INVENTION

1. Field of the Invention

This invention relates to a field of aqueous film coating of nutritional supplements and pharmaceutical tablets, and is specifically concerned with providing film coatings based on dextrin for coating nutritional supplements, such as vitamin tablets and herbal tablets, and pharmaceutical tablets, such as acetaminophen (APAP), aspirin (ASA), and Ibuprofen.

2. Description of the Prior Art

Hydroxypropyl methylcellulose, maltodextrin, and lactose have all been used in coatings for substrates such as pharmaceutical tablets. For example, such coatings made from coating compositions manufactured by Colorcon and disclosed in U.S. Pat. Nos. 4,543,370, 4,683,256, 4,643,894, 4,725,441, and 4,828,841, and 5,630,871 all of said patents being incorporated herein by reference, have proven especially effective when used on pharmaceutical tablets.

However, coatings based on hydroxypropyl methylcellulose, maltodextrin, and lactose, especially clear coats (clear non-pigmented coatings), sometimes suffer from a "frosting" problem (the formation of a white frost-like appearance in the coating) when used to coat nutritional supplements like vitamins and herbal tablets. Also, coatings based on hydroxypropyl methylcellulose, maltodextrin, and lactose sometimes suffer from a "frosting" problem when used to coat pharmaceutical tablets (e.g., color-coded APAP tablets) at a 1% weight gain.

Further, coatings based on hydroxypropyl methylcellulose sometime become too brittle and dried out when used to coat herbal tablets, resulting in coatings peeling off the herbal tablets.

Also, coatings based on hydroxypropyl methylcellulose sometimes have a dull matte finish with low gloss, rather than a desirable glossy finish, when used to coat nutritional supplements like vitamins and herbal tablets.

Tapioca dextrin has been used as an ingredient in a sealant layer for chocolates, nuts, etc. in the food/confectionery field, and the sealant layer containing tapioca dextrin is covered with a coating such as a sugar shell. Tapioca dextrin is recognized to be very brittle and very tacky.

SUMMARY OF THE INVENTION

It is an object of the invention to provide a film coating that possesses long-lasting gloss, good film adhesion, and good film clarity.

Another object of the invention is to provide a film coating that may be used as a gloss coating for vitamin tablets, herbal tablets, and pharmaceutical tablets that possesses long-lasting gloss, that adheres well to difficult substrates such as calcium-oyster shell, and that is non-frosting and clear.

Another object of the invention is to provide a film coating that eases tablet flow in the bed of a coating pan.

These and other objects are accomplished by our invention, which is described below.

DETAILED DESCRIPTION OF THE INVENTION

In accordance with the invention, our dry film coating compositions for use in forming coating suspensions for film coating nutritional supplements, pharmaceutical tablets, and the like, comprise a dextrin and a detackifier.

Advantageously, the inventive dry film coating compositions may include one or more of the following components: auxiliary film-former(s), a plasticizer, a surfactant, colorant, a flow aid, and a preservative.

In accordance with the invention, a method of coating substrates such as nutritional supplements, pharmaceutical tablets, and the like, comprises mixing dextrin and a detackifier into water to form an inventive aqueous coating suspension, applying the inventive coating suspension onto said substrates to form a film coating on said substrates, and drying the film coating on said substrates. Optionally, but advantageously, the following components may be mixed into water with the dextrin and the detackifier to form the inventive coating suspension: auxiliary film-former(s), a plasticizer, a surfactant, colorant, a flow aid, and a preservative.

The invention also includes the coated substrates, such as coated vitamins, coated herbal tablets, and coated pharmaceutical tablets, and the method of making the dry film coating compositions and the method of making the coating suspensions of the invention.

Dextrin $(C_6H_{10}O_5)_n \div H_2O$) is an incompletely hydrolyzed starch. It is prepared by dry heating corn, waxy maize, waxy milo, potato, arrowroot, wheat, rice, tapioca, or sago starches, or by dry heating the starches after treatment with safe and suitable alkalis, acids, or pH control agents and drying the acid or alkali treated starch. A preferred dextrin is tapioca dextrin.

Preferably, dextrin is about 5% to about 97% by weight of the inventive dry film coating composition and of the non-water ingredients of the inventive aqueous coating suspension.

For clear coatings (coatings without colorant), a range of about 35% to about 75% of dextrin by weight of the inventive dry film coating composition and of the non-water ingredients of the inventive aqueous coating suspension is more preferred, and a range of about 65% to about 75% of dextrin by weight of the inventive dry film coating composition and of the non-water ingredients of the inventive aqueous coating suspension is even more preferred.

For white coatings (coatings containing titanium dioxide as the colorant), a range of about 30% to about 50% of dextrin by weight of the inventive dry film coating composition and of the non-water ingredients of the inventive aqueous coating suspension is more preferred, and a range of about 35% to about 40% of dextrin by weight of the inventive dry film coating composition and of the non-water ingredients of the inventive aqueous coating suspension is even more preferred.

For colored coatings (having lakes, dyes, and the like as a colorant), a range of about 35% to about 75% of dextrin by weight of the inventive dry film coating composition and of the non-water ingredients of the inventive aqueous coating suspension is more preferred, and a range of about 45% to about 55% of dextrin by weight of the inventive dry film coating composition and of the non-water ingredients of the inventive aqueous coating suspension is even more preferred.

Examples of the detackifier are mineral oil, carnauba wax, acetylated monoglycerides (Myvacet), lecithin (Alcolec), and magnesium stearate.

For clear coatings (coatings without colorant), a range of about 1% to about 15% of detackifier by weight of the inventive dry film coating composition and of the non-water ingredients of the inventive aqueous coating suspension is preferred, and a range of about 7.5% to about 10% of detackifier by weight of the inventive dry film coating composition and of the non-water ingredients of the inventive aqueous coating suspension is more preferred.

For white coatings (coatings containing titanium dioxide as the colorant), a range of about 1% to about 15% of detackifier by weight of the inventive dry film coating composition and of the non-water ingredients of the inventive aqueous coating suspension is preferred, and a range of about 2% to about 5% of detackifier by weight of the inventive dry film coating composition and of the non-water ingredients of the inventive aqueous coating suspension is more preferred.

For colored coatings (having lakes, dyes, and the like as a colorant), a range of about 1% to about 10% of detackifier by weight of the inventive dry film coating composition and of the non-water ingredients of the inventive aqueous coating suspension is preferred, and a range of about 2% to about 5% of detackifier by weight of the inventive dry film coating composition and of the non-water ingredients of the inventive aqueous coating suspension is more preferred. When using mineral oil as the detackifier in colored formulations, a range of about 1% to about 7.5% of mineral oil by weight of the inventive dry film coating composition and of the non-water ingredients of the inventive aqueous coating suspension is preferred, and a range of about 2% to about 4% of mineral oil by weight of the inventive dry film coating composition and of the non-water ingredients of the inventive aqueous water suspension is even more preferred, in order to avoid color bleeding of the coating if the amount of titanium dioxide in the coating is low.

The auxiliary film-former(s) may be dextrose, polyvinylpyrrolidone (PVP), hydroxypropyl methylcellulose, methylcellulose, hydroxypropyl cellulose (HPC), sodium carboxymethylcellulose (Sodium CMC), maltodextrin, sodium alginate, propylene glycolaginate (P.Galginate) polyvinyl alcohol (PVA), and combinations thereof. The auxiliary film-former(s) act as strength enhancers for the film coating. Their presence in the coatings help prevent cracking of the film coating, as well as helping to prevent edge wear/chipping of the coated tablet. The preferred and the more preferred ranges for the auxiliary film-former(s) by weight of the inventive dry film forming composition and by weight of the non-water ingredients of the inventive aqueous coating suspension are 0%–about 55% (preferred) and 3.5 to 10% (more preferred) for clear formulations, 5%–50% (preferred) and 5% to 20% (more preferred) for white formulations, and 5 to 50% (preferred) and 5 to 20% (more preferred) for colored formulations. The preferred ranges and the more preferred ranges for various exemplary auxiliary film-former(s) are set out below.

When coating extremely friable tablets with a clear coating made from a clear formulation, a preferred auxiliary film-former is NaCMC in an amount up to 50% by weight of the inventive dry film forming composition and by weight of the non-water ingredients of the inventive aqueous coating suspension, and preferably in an amount of about 40% to about 45% by weight of the inventive dry film forming composition and by weight of the non-water ingredients of the inventive aqueous coating suspension. The NaCMC improves the film strength of the inventive coating, which results in the coated tablet being less friable than the uncoated tablet.

Exemplary of the plasticizer are polyethylene glycol having a molecular weight in the range of 200 to 8000, propylene glycol, glycerine, triacetin, acetyltriethyl citrate, triethyl citrate (Citroflex A2), tributylcitrate (Citroflex 4), and acetyltributylcitrate (Citroflex A4), and the preferred ranges for the plasticizer are set out below, together with preferred and more preferred ranges for various exemplary plasticizers.

Exemplary of the surfactant is POLYSORBATE 80 polysorbate, and the preferred ranges for the surfactant are set out below, together with preferred and more preferred ranges for a exemplary surfactant.

A colorant may be any approved colors, opacifiers, or dyes. For example, the colorant may be FD&C lakes, D&C lakes, titanium dioxide, magnesium carbonate, talc, pyrogenic silica, iron oxides, channel black, riboflavin, carmine 40, ponceau 4R, patent blue V5, caramel, curcumin, annatto, dyes, and combinations thereof. The preferred range and the more preferred range for the colorant (the $TiO_2$) in the white formulations are 20% to 50% (preferred) and 25% to 40% (more preferred) by weight of the inventive coating composition and by weight of the non-water ingredients of the inventive coating suspension. The preferred range and the more preferred range for the colorant in the colored formulations are 0.1% to 40% (preferred) and 15% to 25% (more preferred) by weight of the inventive coating composition and by weight of the non-water ingredients of the inventive coating suspension.

Exemplary of the flow aid is stearic acid, and the preferred ranges and the more preferred ranges for the flow aid are set out below, together with the preferred and the more preferred ranges for stearic acid.

Exemplary of the preservative is sodium citrate, and the preferred ranges for the preservative are set out below, together with the preferred and the more preferred ranges for sodium citrate.

|  | CLEAR | WHITE | PIGMENTED |
|---|---|---|---|
| AUXILIARY FILM FORMERS |  |  |  |
| Preferred | 0–55% | 5–50% | 5–50% |
| More Preferred | 3.5–10% | 5–20% | 5–20% |
| Dextrose |  |  |  |
| Preferred | 0–20% | 25–50% | 5–20% |
| More Preferred | 7.5–10% | 30–35% | 7.5–15% |
| PVP |  |  |  |
| Preferred | 0–10% | 0–10% | 0–10% |
| More Preferred | 3.5–7.5% | 3.5–7.5% | 3.5–7.5% |
| HPMC/Methylcellulose/ HPC |  |  |  |
| Preferred | 0–10% | 5–50% | 5–50% |
| More Preferred | 3.5–7.5% | 5–20% | 5–20% |
| Na Alginate/ PG Alginate |  |  |  |
| Preferred | 0–10% | 1–10% | 1–10% |
| More Preferred | 3.5–7.5% | 3.5–7.5% | 3.5–7.5% |
| Na CMC |  |  |  |
| Preferred | 0–50% | 1–10% | 1–10% |
| More Preferred for tablets with low friability | 3.5–7.5% | 3.5–7.5% | 3.5–7.5% |
| More Preferred for tablets with high friability | 40–45% | 3.5–7.5% | 3.5–7.5% |
| Maltodextrin |  |  |  |
| Preferred | 0–25% | 5–50% | 5–50% |
| More Preferred | 15–20% | 5–20% | 5–20% |
| SURFACTANT |  |  |  |
| Preferred Polysorbate 80 | 0–15% | 0–15% | 0–15% |
| Preferred | 0–2% | 0–2% | 0–2% |
| More Preferred | 0.5–1% | 0.5–1% | 0.5–1% |
| FLOW AID |  |  |  |
| Preferred | 0–10% | 0–10% | 0–10% |
| More Preferred | 2–5% | 2–5% | 2–5% |
| Stearic Acid |  |  |  |
| Preferred | 0–10% | 0–10% | 0–10% |
| More Preferred | 2–5% | 2–5% | 2–5% |
| PLASTICIZER |  |  |  |
| Preferred Polyethylene Glycol 8000 | 0–15% | 0–15% | 0–15% |
| Preferred | 0–15% | 0–15% | 0–15% |
| More Preferred | 7.5–10% | 7.5–10% | 7.5–10% |
| Glycerine |  |  |  |
| Preferred | 0–10% | 0–10% | 0–10% |
| More Preferred | 3.5–7.5% | 3.5–7.5% | 3.5–7.5% |
| PRESERVATIVE |  |  |  |
| Preferred Sodium Citrate | 0–5% | 0–5% | 0–5% |
| Preferred | 0–4% | 0–4% | 0–4% |
| More Preferred | 1–2% | 2–3% | 2–3% |

The ranges set out above are all by weight of the dry film coating composition of the invention and of the non-water ingredients of the aqueous coating suspension of the invention.

The following examples illustrate the invention, all ingredients being by weight.

EXAMPLE 1

The dry components of the following formulation were blended together for five minutes in a food processor to form a mixture. Then, the liquid components were added to the mixture of dry components and blended therein by mixing for an additional two minutes.

Optionally, the components of the formulation are granulated using a planetary mixer, such as a Hobart planetary mixer. After the dry film coating composition is loaded into the mixer and the mixer is switched on, sufficient water is slowly added until the composition forms slightly adherent granules. These granules are then passed through a 1–2 mm screen and then dried in a 30° C. oven until the moisture content is below 5%. The composition is then sieved again through a 1–2 mm screen and is then ready for use in a non-dusting, granular form. If not optionally granulated, the composition may be milled such as in a hammer mill (Apex Machinery, Dartford, England), for example.

Other methods of granulation which may be used are spray granulation and roller compaction.

20 grams of the resulting film coating composition was dispersed into 180 grams of distilled water to form an inventive coating solution/suspension (10% solids), and 30 grams of this solution/suspension was sprayed using an Aeromatic Strea I coater onto 1000 grams of color-coated placebos to form the inventive coating thereon having a theoretical weight gain of 1.0%.

This produced a film coating on the tablet that possessed an excellent long-lasting shiny gloss, minimal tackiness, good film adhesion, good non-frosty film clarity.

The above-described coating procedure was repeated, except that a 15% solids coating solution/suspension was used, obtained by mixing 30 grams of the formulation of this example into 170 grams of distilled water to form the aqueous coating solution/suspension, and then spraying 20 grams of the solution/suspension onto 1000 grams of color-coated placebos. Again, the resulting coating possessed an excellent long-lasting shiny gloss, minimal tackiness, good film adhesion, and good non-frosty film clarity.

| Component | Percentages | Grams |
|---|---|---|
| Tapioca Dextrin (A.E. Staley) | 70% | 700.00 |
| Dextrose (A.E. Staley) | 10% | 100.00 |
| Mineral Oil (Eastech Chemical Inc.) | 10% | 100.00 |
| Polyethylene Glycol 8000 (Union Carbide) | 8% | 80.00 |
| Sodium Citrate, Anhydrous | 2% | 20.00 |
| (ADM Corn Processing) | 100% | 1000 |

Examples 2–20 further illustrate the invention, all percentages being by weight.

In Examples 2–12, the components of each formulation are mixed together, formed into a coating suspension, and applied to tablets, as in Example 1, to obtain film coatings possessing long-lasting gloss, good film adhesion, and good film clarity.

EXAMPLE 2

| Component | Percentages | Grams |
|---|---|---|
| Tapioca Dextrin (A.E. Staley) | 72% | 720.00 |
| Dextrose (A.E. Staley) | 10% | 100.00 |
| Mineral Oil (Pennreco) | 15% | 150.00 |
| Sodium Citrate, Anhydrous (ADM Corn Processing) | 2% | 20.00 |
| Polysorbate 80 | 1% | 10.00 |
| (ICI Surfactants) | | |
| | 100% | 1000 |

EXAMPLE 3

| Component | Percentages | Grams |
|---|---|---|
| Tapioca Dextrin (A.E. Staley) | 72% | 720.00 |
| Dextrose (A.E. Staley) | 10% | 100.00 |
| PVP (Pennreco) | 5% | 50.00 |
| Mineral Oil (Pennreco) | 10% | 100.00 |
| Sodium Citrate, Anhydrous (ADM Corn Processing) | 2% | 20.00 |
| Polysorbate 80 | 1% | 10.00 |
| (ICI Surfactants) | | |
| | 100% | 1000 |

EXAMPLE 4

| Component | Percentages | Grams |
|---|---|---|
| Tapioca Dextrin (A.E. Staley) | 69.5% | 695.00 |
| Dextrose (A.E. Staley) | 10% | 100.00 |
| HPMC E-15 (DOW) | 7.5% | 75.00 |
| Mineral Oil (Pennrecc) | 10% | 100.00 |
| Sodium Citrate, Anhydrous (ADM Corn Processing) | 2% | 20.00 |
| Polysorbate 80 | 1% | 10.00 |
| (ICI Surfactants) | | |
| | 100% | 1000 |

EXAMPLE 5

| Component | Percentages | Grams |
|---|---|---|
| Tapioca Dextrin (A.E. Staley) | 63.5% | 635.00 |
| Dextrose (A.E. Staley) | 10% | 100.00 |
| PVP (Pennreco) | 5% | 50.00 |
| Mineral Oil (Pennreco) | 10% | 100.00 |
| Glycerin | 8% | 80.00 |
| Sodium Citrate, Anhydrous (ADM Corn Processing) | 2% | 20.00 |
| Carnauba Wax (Ross) | 1.5% | 15.00 |
| | 100% | 1000 |

EXAMPLE 6

| Component | Percentages | Grams |
|---|---|---|
| Tapioca Dextrin (A.E. Staley) | 38% | 380.00 |
| Sodium CMC (Aqualon) | 18% | 180.00 |
| Dextrose (A.E. Staley) | 16% | 160.00 |
| Maltodextrin (A.E. Staley) | 16% | 160.00 |
| Mineral Oil (Pennreco) | 10% | 100.00 |
| Sodium Citrate, Anhydrous (ADM Corn Processing) | 2% | 20.00 |
| | 100% | 1000 |

EXAMPLE 7

| Component | Percentages | Grams |
|---|---|---|
| Tapioca Dextrin (A.E. Staley) | 95% | 950.00 |
| Mineral Oil (Pennreco) | 5% | 50.00 |
| | 100% | 1000 |

EXAMPLE 8

| Component | Percentages | Grams |
|---|---|---|
| Tapioca Dextrin (A.E. Staley) | 97% | 970.00 |
| Carnuba Wax | 3% | 30.00 |
| | 100% | 1000 |

EXAMPLE 9

| Component | Percentages | Grams |
|---|---|---|
| Tapioca Dextrin (A.E. Staley) | 97% | 970.00 |
| Magnesium Stearate | 3% | 30.00 |
| | 100% | 1000 |

EXAMPLE 10

| Component | Percentages | Grams |
|---|---|---|
| Tapioca Dextrin (A.E. Staley) | 95% | 950.00 |
| Alcolec | 5% | 50.00 |
| | 100% | 1000 |

EXAMPLE 11

| Component | Percentages | Grams |
|---|---|---|
| Tapioca Dextrin | 37.9% | 379 |
| Dextrose | 10.1% | 101 |

-continued

| Component | Percentages | Grams |
|---|---|---|
| Alcolec | 10% | 100 |
| Na Citrate | 2% | 20 |
| Na CMC | 40% | 400 |
| | 100% | 1000 |

EXAMPLE 12

| Component | Percentages | Grams |
|---|---|---|
| Tapioca Dextrin | 32.9% | 329 |
| Dextrose | 10.1% | 101 |
| Alcolec | 10% | 100 |
| Na Citrate | 2% | 20 |
| Na CMC | 45% | 450 |
| | 100% | 1000 |

EXAMPLE 13

The dry components of the following formulation were blended together for five minutes in a PK blender (Paterson Kelly) to form a mixture. Then, the liquid components of the formulation were added to the mixture of the dry components via the I-bar of the blender and blended therein by mixing for an additional five minutes.

140 grams of the resulting film coating composition was dispersed into 1260 grams of distilled water and stirred until dispersed (about 20 minutes) to form an inventive coating solution (10% solids), and all of the solution was sprayed using a 24" Accela Cota coater (Thomas Engineering) onto 14 kg of herbal tablets (black walnut tablets from B&C Nutritional Products) to form the inventive coating thereon having a theoretical weight gain of 1.0%.

This produced a film coating on the tablets that possessed long-lasting gloss, good film adhesion, and good film clarity.

The above-described coating procedure was repeated, except that a 15% solids coating solution was used, obtained by mixing 140 grams of the formulation of this example into 793.33 grams of distilled water to form the aqueous coating solution. Again, the resulting coating possessed long-lasting gloss, good film adhesion, and good film clarity.

| Component | Percentages | Grams |
|---|---|---|
| Tapioca Dextrin (A.E. Staley) | 70% | 3500.00 |
| Dextrose (A.E. Staley) | 10% | 500.00 |
| Mineral Oil (Eastech Chemical Inc.) | 10% | 500.00 |
| Polyethylene Glycol 8000 (Union Carbide) | 8% | 400.00 |
| Sodium Citrate, Anhydrous | 2% | 100.00 |
| (ADM Corn Processing) | | |
| | 100% | 5000 |

EXAMPLE 14

In this example, the components of the formulation of Example 13 are mixed together, formed into a coating suspension, and applied to tablets, as in Example 13, to obtain film coatings possessing long-lasting gloss, good film adhesion, and good film clarity, except that the tablets are vitamins (Pharmavite) rather than herbals.

EXAMPLE 15

In this example, the components of the formulation of Example 13 are mixed together, formed into a coating suspension, and applied to tablets, as in Example 13, to obtain film coatings possessing long-lasting gloss, good film adhesion, and good film clarity, except that the tablets are oyster shell (Delavau) rather than herbals.

EXAMPLE 16

In this example, the components of the formulation of Example 13 are mixed together, formed into a coating suspension, and applied to tablets, as in Example 13, to obtain film coatings possessing long-lasting gloss, good film adhesion, and good film clarity, except that the tablets are APAP rather than herbals.

EXAMPLE 17

(Pearl White)

In this example, the components of the formulation of this example are mixed together, formed into a suspension, and applied to tablets as in Example 13, to obtain non-tacky, smooth film coatings possessing long-lasting, very shiny gloss, good film adhesion, and good film clarity, except that 450 grams of the coating composition of this example was dispersed into 1800 grams of distilled water and stirred until dispersed (about 30 minutes) to form the inventive coating dispersion, and all of the dispersion was sprayed onto 15 kg of vitamins (Pharmavite), rather than 14 kg of herbal tablets, to obtain a theoretical 3.0% weight gain (20% solids).

| Component | Percentages | Grams |
|---|---|---|
| Tapioca Dextrin (Staley) | 39% | 1950.00 |
| HPMC/Pharmacoat E-50 (DOW/ShinEtsu) | 10% | 500.00 |
| Polyethylene Glycol 8000 (Union Carbide) | 8% | 400.00 |
| HPMC/Pharmacoat E-15 (DOW/ShinEtsu) | 5% | 250.00 |
| Sodium Citrate, Anhydrous (ADM Corn Processing) | 3% | 150.00 |
| Mineral Oil (Pennreco) | 3% | 150.00 |
| Titanium dioxide | 32% | 1600.00 |
| (water) (Kronos) | | |
| | 100% | 5000 |

EXAMPLE 18

(Orange)

In this example, the components of the formulation of this example are mixed together, formed into a coating suspension, and applied to tablets, as in Example 17 to obtain film coatings possessing long-lasting gloss, good film adhesion, and good film clarity, except that the coated tablets were provided with a clear overcoat made from dispersing 37.5 grams of the formulation of Example 1 into 212.5 grams of distilled water, and applying said clear overcoat solution as in Example 1 onto the coated tablets of this example for a theoretical 0.25% weight gain at 15% solids. This resulted in a clear overcoat over the colored coating of the invention having a very nice gloss.

| Component | Percentages | Grams |
|---|---|---|
| Tapioca Dextrin (Staley) | 43.55% | 2177.50 |
| Polyethylene Glycol 8000 (Union Carbide) | 8% | 400.00 |
| HPMC/Pharmacoat E-50 (DOW/ShinEtsu) | 10% | 500.00 |
| HPMC/Pharmacoat E-15 (DOW/ShinEtsu) | 5.31% | 265.50 |
| Mineral Oil (Pennreco) | 3% | 150.00 |
| FD&C Yellow No. 6, HT 15–18% | 0.62% | 31.00 |
| Titanium dioxide (water) (Kronos) | 29.52% | 1476.00 |
|  | 100% | 5000 |

EXAMPLE 19
(Red)

The components of the formulation of this example are mixed together, formed into a coating suspension, and applied to tablets, as in Example 17 to obtain film coatings possessing long-lasting gloss, good film adhesion, and good film clarity, except that 450 grams of coating composition of this example was dispersed in 2550 grams of distilled water to form the inventive coating dispersion. As in Example 18, a clear overcoat is applied to the coated tablets of this example following the procedures set out in Example 18, resulting in a clear overcoat over the inventive colored coating on the coated tablets which had a very nice gloss.

| Component | Percentages | Grams |
|---|---|---|
| Tapioca Dextrin (Staley) | 50% | 2500.00 |
| Polyethylene Glycol 8000 (Union Carbide) | 10% | 500.00 |
| HPMC/Pharmacoat E-50 (DOW/ShinEtsu) | 8% | 400.00 |
| Stearic Acid (Witco) | 4% | 200.00 |
| Alcolec F-100 (American Lecithin) | 3% | 150.00 |
| Sodium Alginate (Kelco) | 5% | 250.00 |
| Titanium dioxide (water) (Kronos) | 5.05% | 252.50 |
| FD&C Red No. 40, HT, 38–42% | 13.53% | 676.50 |
| FD&C Blue No. 2, HT, 3–5% | 1.42% | 71.00 |
|  | 100% | 5000 |

EXAMPLE 20
(Maroon)

In this example, the components of the formulation of this example are mixed together, formed into a suspension, and applied to tablets as in Example 13, to obtain film coatings possessing long-lasting gloss, good film adhesion, and good film clarity.

| Component | Percentages | Grams |
|---|---|---|
| Tapioca Dextrin | 29% | 1450.00 |
| Dextrose | 10% | 500.00 |
| PEG 8000 | 10% | 500.00 |
| Stearic Acid | 4% | 200.00 |
| HPMC E-50 | 8% | 400.00 |
| Alcolec F-100 | 3% | 150.00 |
| Sodium Alginate XL | 5% | 250.00 |
| FD&C Red No. 40, HT, 38–42% | 24.56% | 1228.00 |
| Titanium Dioxide | 4.43% | 221.50 |
| FD&C Blue No. 2, HT, 11–15% | 2.01% | 100.50 |
|  | 100% | 5000 |

"Slit" Phenomenon

The inventive film coating causes a unique phenomenon, the reduction of the coefficient of tablet friction, which we refer to as "slip factor" or "slip". The inventive film coating reduces the coefficient of friction of the tablets, thereby reducing the friction between tablets, both during and after application of the coating onto the tablets, such that the tablets slide or glide or slip past each other as they tumble in the coating pan during application of the film coating and as they are poured during packaging procedures after being coated. In other words, the inventive film coating imparts a slipperiness onto the tablet and permits the tablets to flow more easily over one another.

We have discovered that the inventive film coating causes a reduction of the coefficient of tablet friction. With a reduction of the coefficient of tablet friction, tablets flow better in the bed of a coating pan creating space for more tablets to be placed in the coating pan to be coated with the inventive coating. To maintain the optimum bed geometry and bed flow desired for coating the tablets in the coating pan, a larger tablet charge (10–20% increase in pan load) is used when coating with the inventive coating. Accordingly, an increase in productivity is achieved since more tablets are coated at once.

Further, tablets provided with "slip" (that is, tablets having a reduced coefficient of tablet friction) slide/glide past each other, which is particularly advantageous when coating bulky tablets and tablets having friable edges that have a tendency to chip off as the tablets tumble in the coating pan.

Tablets with "slip" also increase productivity by lessening the time needed for processing the coated tablets from the coating pan to packaging of the coated tablets since tablets with the inventive film coating flow better than tablets coated with other film coatings.

The following Tests 1, 2, and 3 were conducted to compare "slip" obtained from the inventive film coating with "slip" (if any) obtained from other film coatings. Film coatings (3% weight gain) having the following coating formulations were used in each test:

| Formulation A (An OPADRY Coating Composition) | |
|---|---|
| Component | Portion by weight |
| HPMC 6 CPS-Methocel E-6 | 31.720 |
| HPMC 3 CPS-Methocel E-3 | 31.720 |
| Titanium Dioxide (water) | 26.410 |
| Peg 400 NF | 8.000 |
| FD&C Yellow No. 6 HT 15%–18% | 1.150 |
| Polysorbate 80 NF | 1.000 |
|  | 100.000 |

Formulation B
(An OPADRY II Coating Composition)

| Component | Portion by weight |
|---|---|
| HPMC 3 CPS-Methocel E-3 | 30.330 |
| Titanium Dioxide (water) | 29.450 |
| Maltodextrin (Star-Dri 5) | 18.000 |
| HPMC 6 CPS-Methocel E-6 | 9.340 |
| Triacetin USP/EP/JPE-Eastman | 7.500 |
| Peg 8000 NF | 2.500 |
| HPMC-Methocel E50-LV Premium | 2.330 |
| FD&C Yellow No. 6 HT 15%–18% | .550 |
| | 100.000 |

Formulation C
(An OPADRY II Coating Composition)

| Component | Portion by weight |
|---|---|
| Titanium Dioxide (water) | 31.200 |
| Polydextrose powder | 23.600 |
| HPMC 3 CPS-Methocel E-3 | 15.200 |
| HPMC 6 CPS-Methocel E-6 | 15.200 |
| Triacetin USP/EP/JPE-Eastman | 6.000 |
| HPMC-Methocel E50-LV Premium | 5.000 |
| Peg 8000 NF | 2.000 |
| FD&C Yellow No. 6 HT 15%–18% | 1.800 |
| | 100.000 |

Formulation D
(An OPADRY II Coating Composition)

| Component | Portion by weight |
|---|---|
| Lactose Monohyd. #316, NF, FF | 40.000 |
| HPMC 15 CP-Pharmacoat 615 | 28.000 |
| Titanium Dioxide (water) | 22.500 |
| Triacetin USP/EP/JPE-Eastman | 8.000 |
| FD&C Yellow No. 6 HT 15%–18% | 1.500 |
| | 100.000 |

Formulation E
(An OPADRY XD Coating Composition)

| Component | Portion by weight |
|---|---|
| Titanium Dioxide (water) | 30.860 |
| Dextrose | 28.084 |
| Maltodextrin (Star-Dri 1) | 21.216 |
| Sodium Alginate Kelgin-XL | 5.440 |
| HPMC 15 CPS-Methocel E-15 | 5.100 |
| Triacetin USP/EP/JPE/Eastman | 4.760 |
| Stearic Acid PDR (Kosher) | 2.720 |
| FD&C Yellow No. 6 HT 15%–18% | 1.140 |
| Alcolec F-100 | .680 |
| | 100.000 |

Formulation F
(An OPADRY NS Coating Composition)

| Component | Portion by weight |
|---|---|
| Titanium Dioxide (water) | 36.516 |
| Tapioca Dextrin 955 SR | 30.670 |
| HPMC-Methocel E50-LV Premium | 10.000 |
| Peg 8000 NF | 7.000 |
| PB-15Y-Y6-17 | 4.768 |
| HPMC 15 CPS-Methocel E-15 | 4.046 |
| Alcolec F-100 | 4.000 |
| Peg 400 NF | 3.000 |
| | 100.000 |

Formulation F is an exemplary formulation for the inventive film coating.

Test 1—Measurement of Flow Rate

A first set of vitamins was coated with a film coating using Formulation A, a second set of vitamins was coated with a film coating using Formulation B, a third set of vitamins was coated with a film coating using Formulation C, a fourth set of vitamins was coated with a film coating using Formulation D, a fifth set of vitamins was coated with a film coating using Formulation E, and a sixth set of vitamins was coated with a film coating using Formulation F. The flow rate for each set of coated vitamins was then measured using the following procedure to determine which film coating provided the highest flow rate.

For each set of vitamins, the chamber of a Flodex Tester flow meter (manufactured by Hanson Research) was filled with the coated vitamins, but without packing the tablets down into the chamber. Then, the release lever for the release door of the Flodex Tester flow meter was pulled to release the tablets from the chamber through a 46 mm orifice, and the time was measured from the start of tablet flow to the end of tablet flow. This procedure was followed 5 times for each set of vitamins, and the average length of time of flow and the standard deviation were determined. A constant weight (in this test 173 grams of vitamin tablets) of vitamins was used throughout the testing. The vitamin tablets coated with film coatings made using Formulations A, B, and D did not flow from the Flowdex Tester's chamber unassisted, but rather needed to be coerced into flowing by banging on the side of the Flodex Tester's chamber.

The results of this test are shown in Table 1(a).

TABLE 1(a)

| Formulation | Time (seconds) | Standard Deviation |
|---|---|---|
| A | 1.674 | 1.0735 |
| B | 2.082 | 0.6543 |
| C | 1.302 | 0.1572 |
| D | 1.824 | 1.0211 |
| E | 1.36 | 0.1325 |
| F | 1.04 | 0.1736 |

A seventh set of vitamins was coated (3% weight gain) with a film coating using an exemplary formulation (Formulation G) for the inventive film coating. Then, a first subset of these Formulation G coated vitamins was coated with a gloss coat (0.25% weight gain) using Formulation H, and a second subset of Formulation G coated vitamin tablets was coated with a clear gloss coat (0.25% weight gain) using Formulation I, which is an exemplary formulation for the inventive film coating. The flow rate for the coated vitamins provided with a clear gloss coat based on Formulation H and the flow rate for the coated vitamins provided with a gloss coat based on Formulation I were then measured using the Test 1 procedure set out above to determine which vitamins have the highest flow rate. The results are shown in Table 1(b).

Formulation G
(An OPADRY NS Coating Composition)

| Component | Portion by weight |
|---|---|
| Tapioca Dextrin | 31.500 |
| Dextrose | 7.500 |
| HPMC E-50 | 12.000 |
| HPMC E-15 | 10.000 |
| Alcolec F-100 | 4.000 |
| PEG 8000 | 7.000 |
| PEG 400 | 3.000 |
| $TiO_2$ | 3.720 |
| FD&C Red No. 40 HT 38–42% | 19.190 |
| FD&C Blue No. 2 HT 11–14% | 2.090 |
| | 100.000 |

Formulation H
(An OPADRY Clear Coating Composition)

| Component | Portion by weight |
|---|---|
| HPMC 6 CPS-Pharmacoat 606 | 90.900 |
| PEG 400 NF | 4.550 |
| PEG 8000 NF | 4.550 |
| | 100.000 |

Formulation I
(An OPADRY NS Coating Composition)

| Component | Portion by weight |
|---|---|
| Tapioca Dextrin 955 SR | 72.900 |
| Dextrose | 10.100 |
| Alcolec F-100 | 10.000 |
| Sodium CMC | 5.000 |
| Sodium Citrate, FCC, USP | 2.000 |
| | 100.000 |

TABLE 1(b)

| Formulation | Time (sec.) |
|---|---|
| H | 1.36 |
| I | 1.26 |

As shown by the above test results, vitamin tablets coated with the inventive film coating (Formulation F and Formulation I) flowed better than the vitamin tablets coated with the other film coatings, illustrating the slip factor provided by the inventive film coating.

Test 2—Angle of Repose

A first set of vitamins was coated with a film coating using Formulation A, a second set of vitamins was coated with a film coating using Formulation B, a third set of vitamins was coated with a film coating using Formulation C, a fourth set of vitamins was coated with a film coating using Formulation D, a fifth set of vitamins was coated with a film coating using Formulation E, and a sixth set of vitamins was coated with a film coating using Formulation F.

The angle of repose for each set of coated vitamins was then measured using the following procedure.

For each set of vitamins, 1.0 kg of vitamins were placed in a funnel having a 2.75 cm diameter orifice, which was initially plugged. The funnel was supported in a support ring mounted on a stand such that the bottom of the funnel was 4½ inches above a countertop. With the vitamins in place in the funnel, the stopper was removed from the orifice to permit the tablets to flow from the funnel through the orifice to form a pile of tablets on the countertop. The angle of the pile (the angle of the repose) was measured. This procedure was followed three times for each set of vitamins, and the average angle of repose for each set of vitamins was determined. The set of tablets coated with the inventive film coating (Formulation F) was the only set of tablets that flowed uninhibited through the funnel.

The results of this test are shown in Table 2.

TABLE 2

| Formulation | Angle of Repose (degrees) |
|---|---|
| A | 44.33 |
| B | 41.33 |
| C | 41.67 |
| D | 40.67 |
| E | 29 |
| F | 20 |

As shown by the above test results, vitamin tablets coated with the inventive film coating (Formulation F) created the smallest angle of repose illustrating the slip factor provided by the inventive film coating.

Test 3—Measurement of Degree Differential

A first set of vitamins was coated with a film coating using Formulation A, a second set of vitamins was coated with a film coating using Formulation B, a third set of vitamins was coated with a film coating using Formulation C, a fourth set of vitamins was coated with a film coating using Formulation D, a fifth set of vitamins was coated with a film coating using Formulation E, and a sixth set of vitamins was coated with a film coating using Formulation F.

A seventh set of vitamins was coated (3% weight gain) with a film coating using an exemplary formulation (Formulation G) for the inventive film coating. Then, a first subset of these Formulation G coated vitamins was coated with a gloss coat (0.25% weight gain) using Formulation H, and a second subset of these Formulation G coated vitamins was coated with a gloss coat (0.25% weight gain) using Formulation I, which is an exemplary formulation of the inventive film coating.

The degree differential for each set (sets 1–6 and subsets 1 and 2 of set 7) of coated vitamins was measured using the following procedure to establish numerical data on slip. The degree differential is the degree of drop between the top of a tablet bed of uncoated tablets and the top of a tablet bed of coated tablets.

Figure 1:
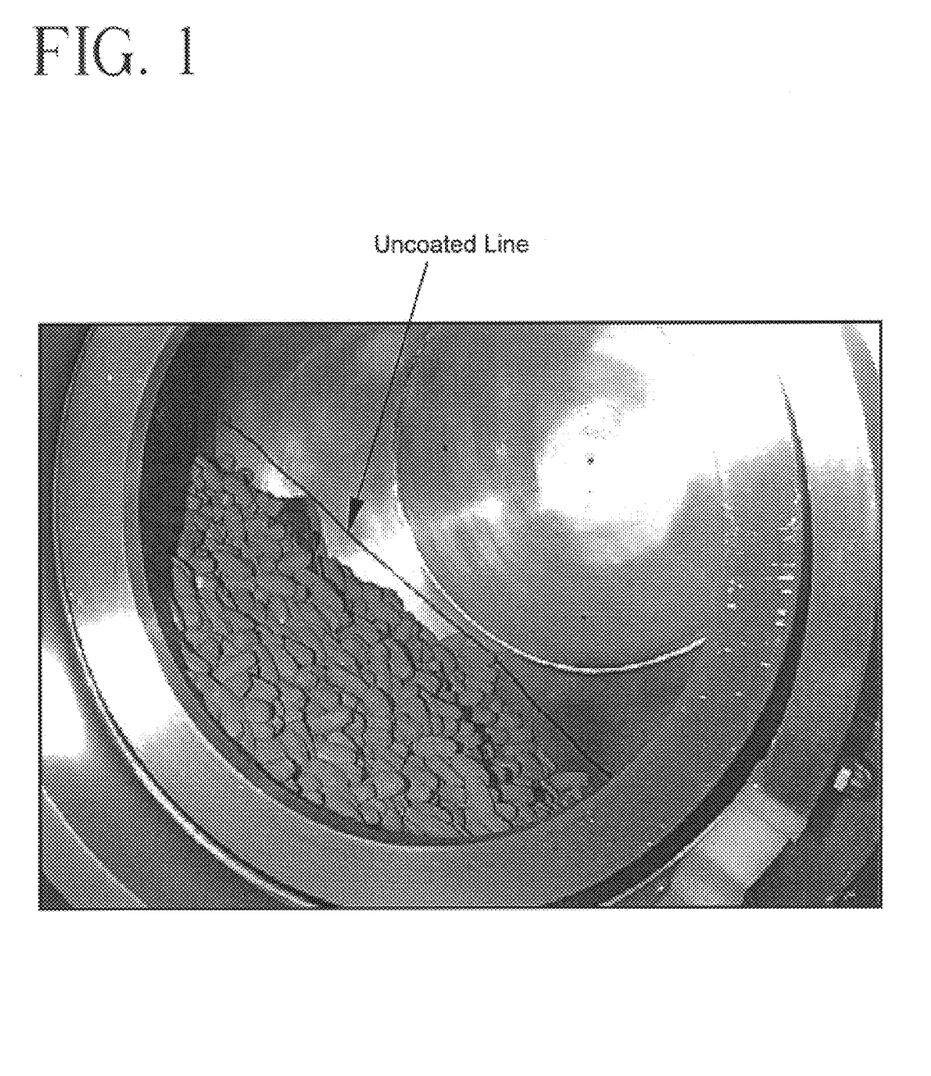
FIG. 1 shows a coating pan containing 3.5 kg of uncoated tablets. A line is drawn on the back wall of the coating pan which follows the plane bordering and parallel to the top of the tablet bed of the uncoated tablets.
Figure 2:
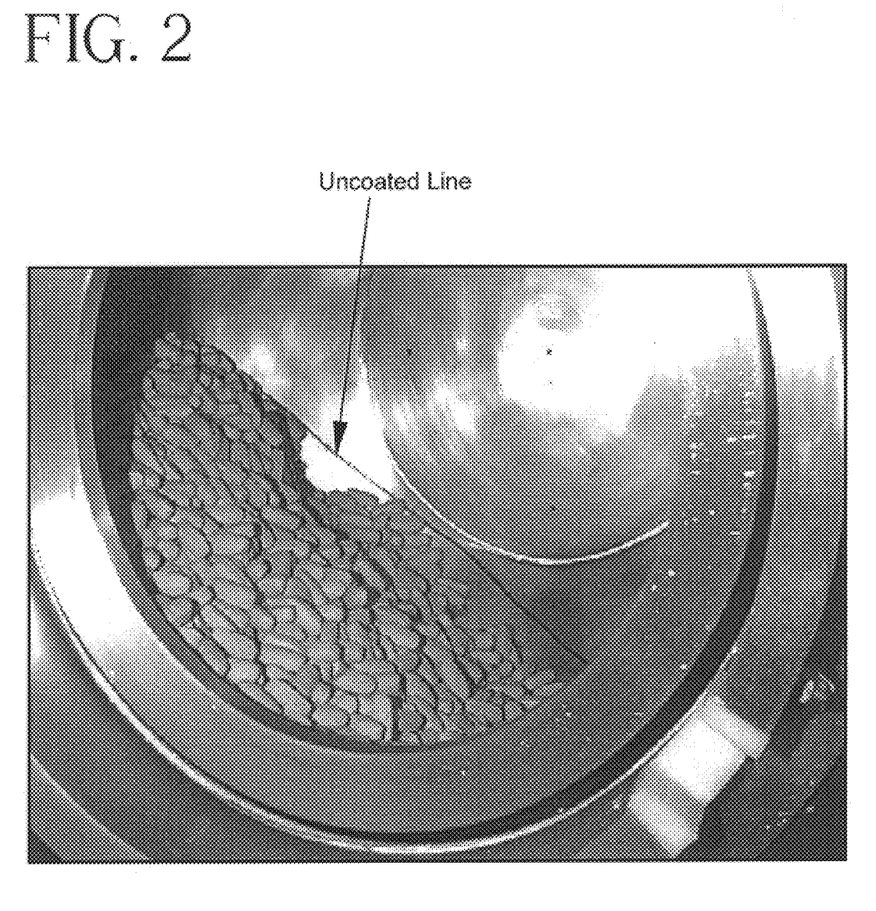
FIG. 2 shows a coating pan containing 3.5 kg of tablets coated with a film coating made using Formulation A. This figure illustrates that the bed geometry for the coated tablets matches the bed geometry of the uncoated tablets shown in FIG. 1.
Figure 3:
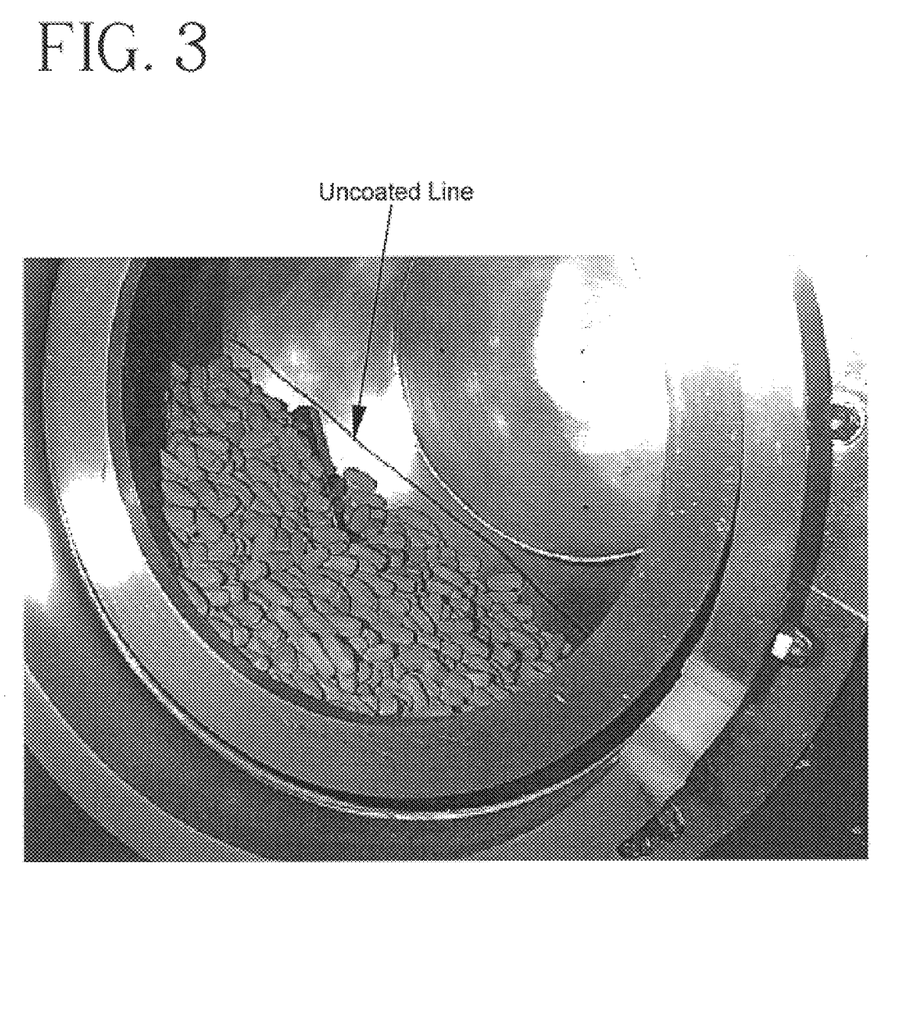
FIG. 3 shows a coating pan containing 3.5 kg of tablets coated with a film coating made using Formulation B. This figure illustrates that the bed geometry for the coated tablets matches the bed geometry of the uncoated tablets shown in FIG. 1.
Figure 4:
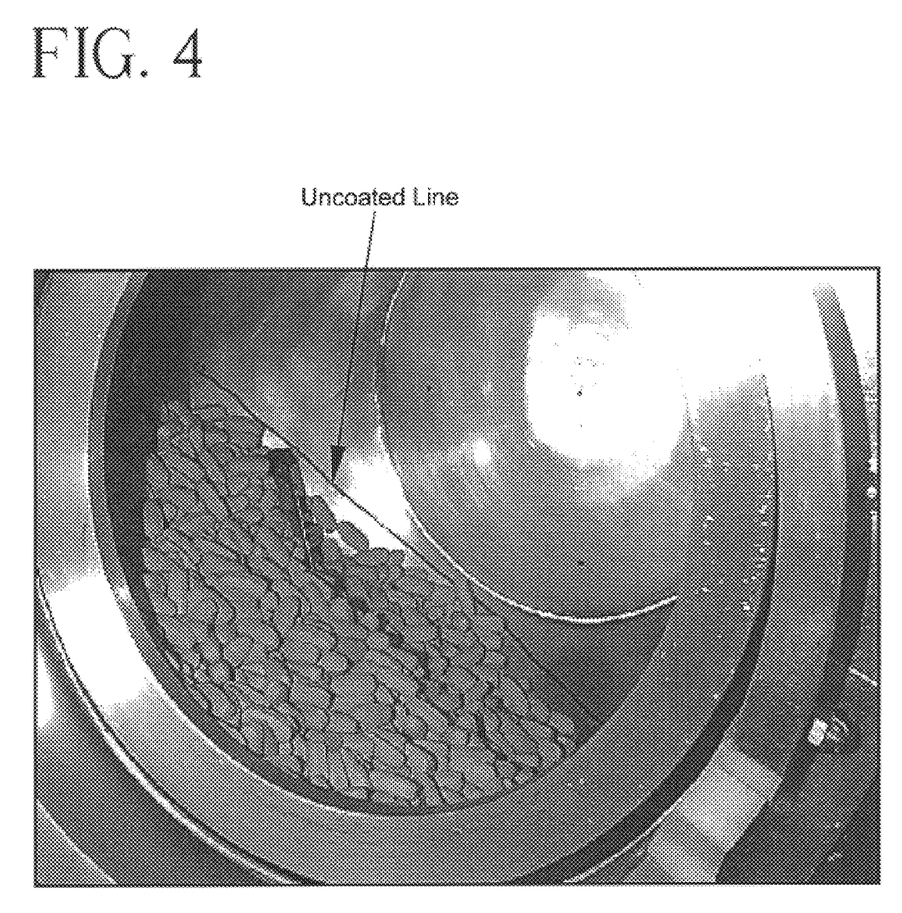
FIG. 4 shows a coating pan containing 3.5 kg of tablets coated with a film coating made using Formulation C. This figure illustrates that the bed geometry for the coated tablets matches the bed geometry of the uncoated tablets shown in FIG. 1.
Figure 5:
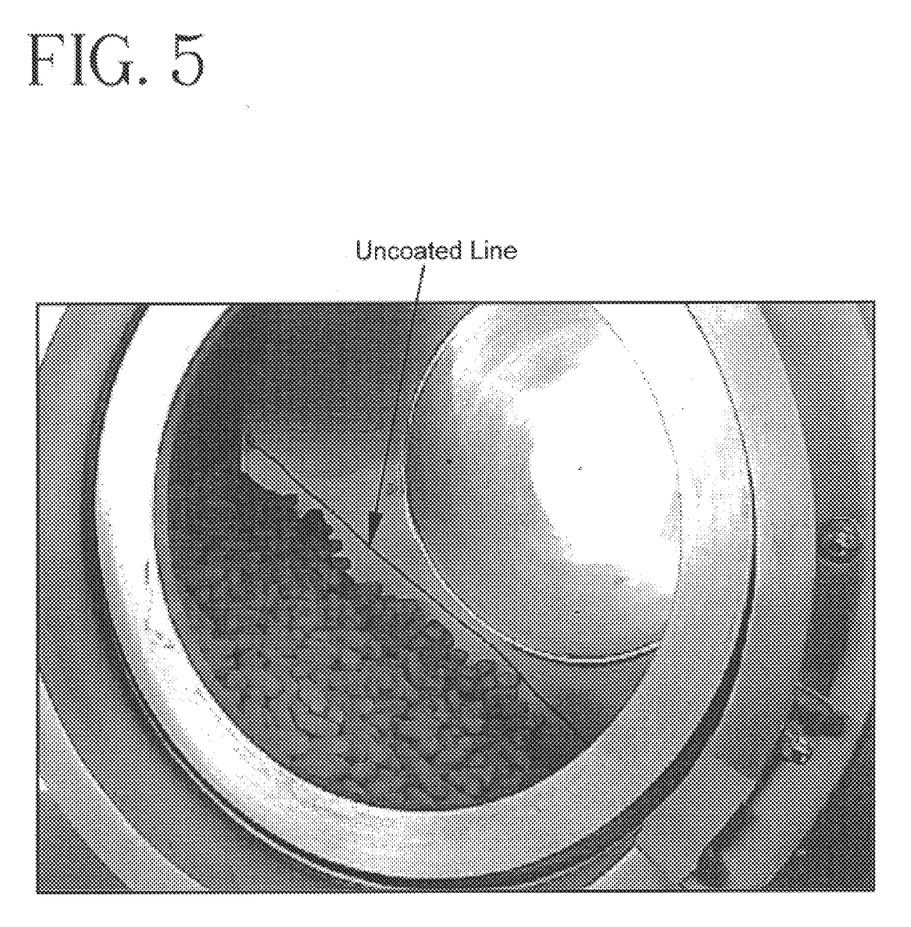
FIG. 5 shows a coating pan containing 3.5 kg of tablets coated with a film coating made using Formulation D. This figure illustrates that the bed geometry for the coated tablets matches the bed geometry of the uncoated tablets shown in FIG. 1.
Figure 6:
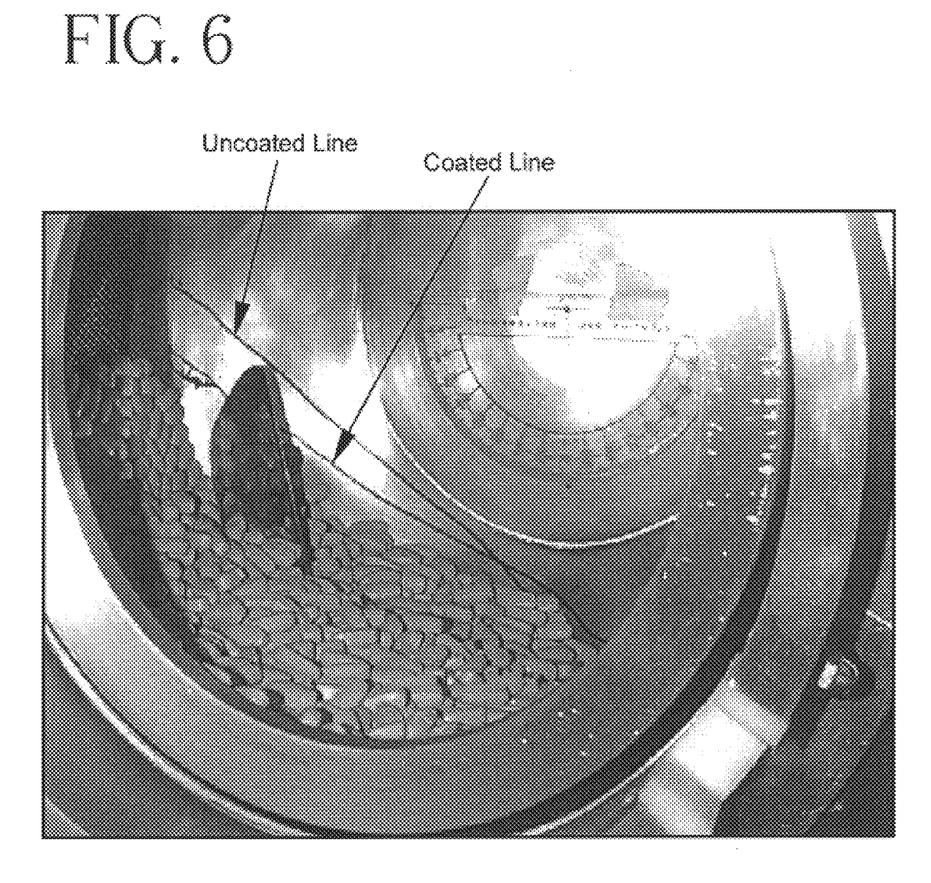
FIG. 6 shows a coating pan containing 3.5 kg of tablets coated with a film coating made using Formulation E. This figure illustrates a slight drop in the tablet bed geometry compared with the tablet bed geometry shown in FIG. 1.
Figure 7:
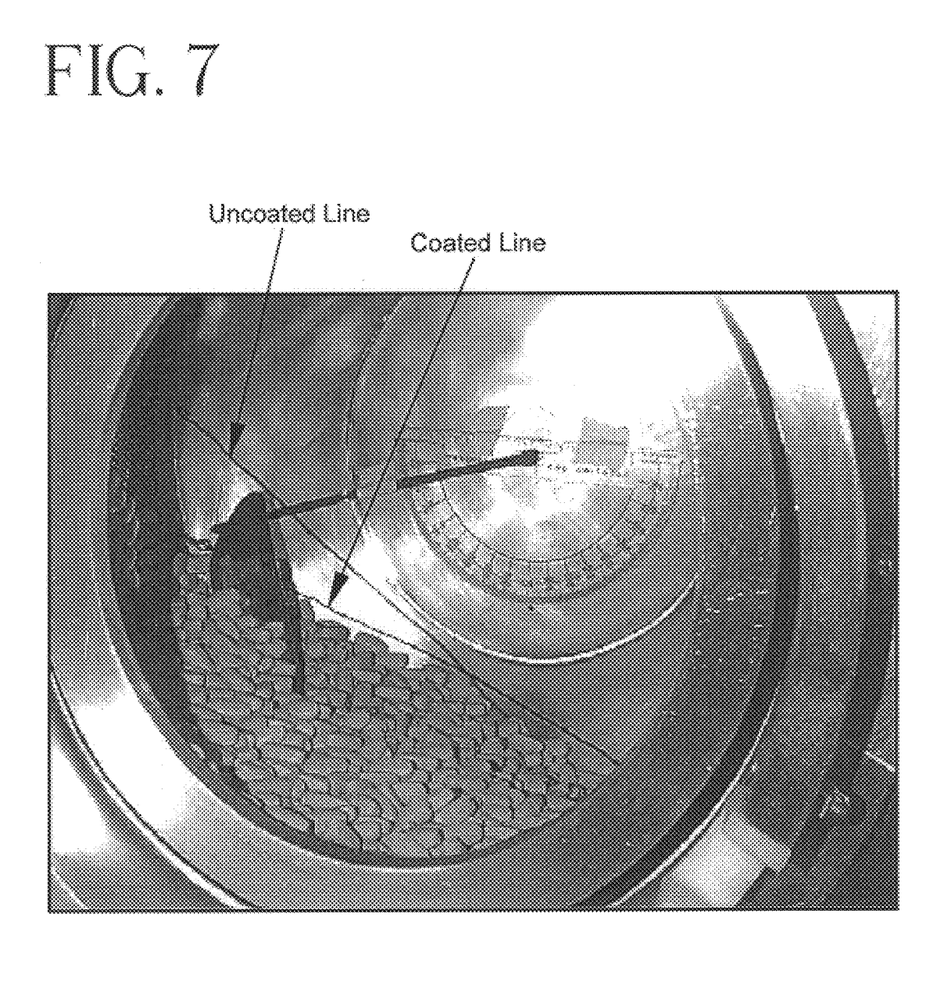
FIG. 7 shows a coating pan containing 3.5 kg of tablets coated with a film coating made using Formulation F. This figure illustrates a significant drop in the tablet bed geometry compared with the tablet bed geometry shown in FIG. 1.

3.5 kg of uncoated vitamins were placed in a O'Hara Labcoat I coating pan (a 15 inch pan), and the uncoated tablets were tumbled in the coating pan for two revolutions at a pan speed of three revolutions per minute. As shown in FIG. 1, a first line was drawn on the back wall of the coating pan following the plane bordering and parallel to the top of the tablet bed of the uncoated tablets.

The uncoated tablets were then removed from the coating pan.

Then, for each set (sets 1–6 and subsets 1 and 2 of set 7) of coated vitamin tablets, 3.5 kg of coated vitamins were placed into the coating pan, and the coated tablets were tumbled in the coating pan for two revolutions at a pan speed of three revolutions per minute. A second line was drawn on the back wall of the coating pan following the plane bordering and parallel to the top of the tablet bed of the coated tablets if the bed geometry did not match the bed geometry of the uncoated tablets marked by the first line.

To determine the degree differential (the degree of drop in the level of the high end of the tablet bed) between uncoated tablets and coated tablets, we measured the angle formed between 1) a horizontal line along the back wall of the coating pan that intersects the end portion of the high end of the uncoated tablet bed and 2) a line from the end portion of the high end of the coated tablet bed to the point on the back wall of the coating pan where the horizontal line mentioned above intersects a vertical line along the back wall of the coating pan that bisects the coating pan.

The test procedure set out above was followed for each set (sets 1–6 and subset 1 and 2 of set 7) of vitamins, and the results of this test are shown in Table 3, and are illustrated in FIGS. 1–7.

Referring to the data in Table 3, and to FIGS. 1–7, film coatings based on Formulations A, B, C, and D did not reduce the coefficient of friction of the tablets, and accordingly, the bed geometry for the coated tablets based on Formulations A, B, C, and D matches the bed geometry of the uncoated tablets, as shown in FIGS. 1–5.

Film coatings based on Formulations E and H only slightly reduced the coefficient of friction of the tablets, and, accordingly, there is only a slight drop in the tablet bed geometry (Degree Differential of only 7 degrees) for coated tablets based on Formulations E (see FIG. 6) and H compared with the tablet bed geometry for uncoated tablets.

Film coatings based on Formulations F and I made in accordance with the invention significantly reduced the coefficient of friction of the tablets, and, accordingly, there is a significant drop in the tablet bed geometry (Degree Differential of 19 degrees for Formulation F (see FIG. 7) and 20 degrees for Formulation I) of the coated tablets based on Formulations F and I compared with the tablet bed geometry for uncoated tablets.

TABLE 3

| Formulation | Degree Differential (degrees) |
|---|---|
| A | 0 |
| B | 0 |
| C | 0 |
| D | 0 |
| E | 7 |
| F | 19 |
| H | 7 |
| I | 20 |

As shown by the above test results, tablets coated with the inventive film coating (Formulation F and I) provided the largest degree differential, illustrating the degree of slip provided thereby.

ADVANTAGES

The invention provides a film coating that possesses long-lasting gloss, good film adhesion, and good film clarity.

Our invention also provides a film coating that may be used as a gloss coating for vitamin tablets, herbal tablets, and pharmaceutical tablets that possesses long-lasting gloss, that adheres well to difficult substrates such as calcium-oyster shell, and that is non-frosty and clear.

The coatings produced in accordance with the invention mask the odor of the substrates coated thereby, which is particularly advantageous when dealing with vitamins and herbal tablets that do not have a pleasant odor.

The inventive coating provides a glossy, elegant finish on pharmaceutical tablets without the need of applying a clear overcoat on the coated colored tablets. However, applying a clear overcoat on the coated-colored tablets coated with the inventive coating further enhances the finish on the tablets.

The inventive coating promotes a very fine logo definition on pharmaceutical tablets.

The inventive aqueous coating solution/suspension/dispersion has a viscosity that is markedly lower than the viscosities of coating suspensions based on hydroxypropyl methylcellulose, and maltodextrin. For example, the viscosity of the formulation of Example 1 at a 30% solids level is 18.5 cP, at 40% solids is 87.5 cP, and at 50% solids is 381 cP. Accordingly, the tablet weight gain due to coating may be reduced to 0.5% to 0.75%, which is substantially lower than the tablet weight gain associated with prior art coating systems, and still obtain a coated tablet having an excellent gloss. Also, due to the lower viscosity of the coating solutions/suspensions/dispersions of the invention, there is less of a likelihood of clogging of spraying equipment during the coating process, and the ability to use higher solids content in the inventive coating suspension than that may be advisable to use in the prior art systems.

The inventive film coating also causes a reduction of the coefficient of tablet friction, and as a result of this, tablets flow better in the bed of a coating pan. Due to this better tablet flow, the pan load may be increased by 10–20% while maintaining the optimum bed geometry and bed flow desired for coating the tablets. Accordingly, an increase in productivity is achieved since more tablets may be coated at once.

Further, with a reduction of the coefficient of tablet friction obtained by the inventive film coating, tablets flow better in the bed of a coating pan which results in a reduction of edge chipping/edge wear during the coating process.

Tablets provided with the inventive "slip" also increase productivity by lessening the time needed to process the coated tablets from the coating pan to packaging of the coated tablets since the tablets with the inventive film coating flow better than tablets coated with other film coatings.

What is claimed is:

1. A dry film coating composition for forming an aqueous coating suspension for film coating nutritional supplements and pharmaceutical tablets, comprising
   5–97% by weight tapioca dextrin, and
   a 1–15% by weight detackifier.

2. The composition of claim 1, wherein the detackifier is selected from the group consisting of:
   mineral oil, carnauba wax, acetylated monoglyceride, lecithin, magnesium stearate, and combinations thereof.

3. The composition of claim 1,
   the tapioca dextrin being 35% to 75% by weight of the composition.

4. The composition of claim 1,
   the tapioca dextrin being 65% to 75% by weight of the composition.

5. The composition of claim 1,
   the detackifier being 7.5% to 10% by weight of the composition.

6. The composition of claim 1, further including an auxiliary film-former.

7. The composition of claim 6, wherein the auxiliary film-former is selected from the group consisting of:

dextrose, polyvinylpyrolidone (PVP), hydropropyl, methylcellulose, hydroxypropyl cellulose (HPC), sodium carboxymethylcellulose (Sodium CMC), maltodextrin, sodium alginate, propylene glycol alginate (PG alginate), polyvinyl alcohol (PVA), and combinations thereof.

8. The composition of claim 6, the auxiliary film-former being in a range of greater than 0% to about 55% by weight of the composition.

9. The composition of claim 6, the auxiliary film-former being in a range of greater than 3.5% to about 10% by weight of the composition.

10. The composition of claim 8, the auxiliary film-former being sodium carboxymethylcellulose (Sodium CMC) in a range of about 40–45% by weight of the composition.

11. The composition of claim 1, further including a plasticizer.

12. The composition of claim 11 wherein the plasticizer is selected from the group consisting of:

polyethylene glycol, propylene glycol, glycerine, triacetin, acetyltriethyl citrate, triethyl citrate, tributylcitrate, and acetyltributylcitrate.

13. The composition of claim 11, the plasticizer being in a range of greater than 0% to about 15% by weight of the composition.

14. The composition of claim 11, the plasticizer being in a range of 7.5% to 10% by weight of the composition.

15. The composition of claim 11, the plasticizer being in a range of 3.5% to 7.5% by weight of the composition.

16. The composition of claim 1, further including a surfactant.

17. The composition of claim 16, the surfactant being polysorbate.

18. The composition of claim 16, the surfactant being in a range of greater than 0% to about 2% by weight of the composition.

19. The composition of claim 16, the surfactant being in a range of greater than 0.5% to about 1% by weight of the composition.

20. The composition of claim 1, further including a flow aid.

21. The composition of claim 20, the flow aid being stearic acid.

22. The composition of claim 20, the flow aid being in a range of greater than 0% to about 10% by weight of the composition.

23. The composition of claim 20, the flow aid being in a range of greater than 2% to about 5% by weight of the composition.

24. The composition of claim 1, further including a preservative.

25. The composition of claim 24, the preservative being sodium citrate.

26. The composition of claim 24, the preservative being in a range of greater than 0% to about 5% by weight of the composition.

27. The composition of claim 24, the preservative being in a range of greater than 1% to about 2% by weight of the composition.

28. The composition of claim 1, further including an auxiliary film-former, and titanium dioxide.

29. The composition of claim 28, the tapioca dextrin being in a range of about 30% to about 50% by weight of the dry film coating composition, the detackifier being in a range of about 1% to about 15% by weight of the dry film coating composition, the auxiliary film-former being in a range of about 5% to about 50% by weight of the dry film coating composition, and the titanium dioxide being in a range of about 20% to about 50% by weight of the dry film coating composition.

30. The composition of claim 28, the topica dextrin being in a range of about 35% to about 40% by weight of the dry film coating composition, the detackifier being in a range of about 2% to about 5% by weight of the dry film coating composition, the auxiliary film-former being in a range of about 5% to about 20% by weight of the dry film coating composition, and the titanium dioxide being in a range of about 25% to about 40% by weight of the dry film coating composition.

31. The composition of claim 28, further including a plasticizer.

32. The composition of claim 28, further including a surfactant.

33. The composition of claim 28, further including a flow aid.

34. The composition of claim 28, further including a preservative.

35. The composition of claim 29, further including a plasticizer, a surfactant, a flow aid, and a preservative, the plasticizer being in a range of about 1% to about 15% by weight of the composition, the surfactant being in a range of about 1% to about 2% by weight of the composition, the flow aid being in a range of greater than 0% to about 10% by weight of the composition, and the preservative being in a range of about 1% to about 4% by weight of the composition.

36. The composition of claim 30, further including a plasticizer, a surfactant, a flow aid, and a preservative, the plasticizer being in a range of about 7.5% to about 10% by weight of the composition, the surfactant being in a range of about 0.5% to about 1% by weight of the composition, the flow aid being in a range of about 2% to about 5% by weight of the composition, and the preservative being in a range of about 2% to about 3% by weight of the composition.

37. The composition of claim 1, further including an auxiliary film-former, and a colorant.

38. The composition of claim 37, the tapioca dextrin being in a range of about 35% to about 75% by weight of the dry film coating composition, the detackifier being in a range of about 1% to about 10% by weight of the dry film coating composition, the auxiliary film-former being in a range of about 5% to about 50% by weight of the dry film coating composition, and the colorant being in a range of about 0.1% to about 40% by weight of the dry film coating composition.

39. The composition of claim 37, the tapioca dextrin being in a range of about 45% to about 55% by weight of the dry film coating composition, the detackifier being in a range of about 2% to about 5% by weight of the dry film coating composition, the auxiliary film-former being in a range of about 5% to about 20% by weight of the dry film coating composition, and the colorant being in a range of about 15% to about 25% by weight of the dry film coating composition.

40. The composition of claim 37, further including a plasticizer.

41. The composition of claim 37, further including a surfactant.

42. The composition of claim 37, further including a flow aid.

43. The composition of claim 37, further including a preservative.

44. The composition of claim 38, further including a plasticizer, a surfactant, a flow aid, and a preservative, the plasticizer being in a range of greater than 0% to about 15% by weight of the composition, the surfactant being in a range of greater than 0% to about 2% by weight of the composition, the flow aid being in a range of greater than 0% to about 10% by weight of the composition, and the preservative being in a range of greater than 0% to about 5% by weight of the composition.

45. The composition of claim 39, further including a plasticizer, a surfactant, a flow aid, and a preservative, the plasticizer being in a range of about 7.5% to about 10% by weight of the composition, the surfactant being in a range of about 0.5% to about 1% by weight of the composition, the flow aid being in a range of about 2% to about 5% by weight of the composition, and the preservative being in a range of about 2% to about 3% by weight of the composition.

* * * * *